US00PP19187P2

(12) United States Plant Patent
O'Donovan

(10) Patent No.: US PP19,187 P2
(45) Date of Patent: Sep. 9, 2008

(54) ***GERANIUM* PLANT NAMED 'OGLGER14010'**

(50) Latin Name: *Pelargonium peltatum*
Varietal Denomination: Oglger14010

(75) Inventor: Wendy Oglevee O'Donovan, Scottdale, PA (US)

(73) Assignee: Ecke Geraniums LLC, Encinitas, CA (US)

( * ) Notice: Subject to any disclaimer, the term of this patent is extended or adjusted under 35 U.S.C. 154(b) by 0 days.

(21) Appl. No.: 11/804,333

(22) Filed: May 17, 2007

(51) Int. Cl.
*A01H 5/00* (2006.01)

(52) U.S. Cl. ..... Plt./332
(58) Field of Classification Search ..... Plt./332
See application file for complete search history.

*Primary Examiner*—Anne Marie Grunberg
*Assistant Examiner*—Louanne C Krawczewicz Myers
(74) *Attorney, Agent, or Firm*—C. A. Whealy

(57) ABSTRACT

A new and distinct cultivar of Ivy *Geranium* plant named 'Oglger14010', characterized by its outwardly spreading plant habit; freely basal branching habit; freely flowering habit; double red and pale pink to white bi-colored flowers; and good garden performance.

1 Drawing Sheet

Botanical designation: *Pelargonium peltatum.*
Cultivar denomination: 'Oglger14010'.

BACKGROUND OF THE INVENTION

The present invention relates to a new and distinct cultivar of Ivy *Geranium*, botanically known as *Pelargonium peltatum,* and hereinafter referred to by the name 'Oglger14010'.

The new Ivy *Geranium* is a product of a planned breeding program conducted by the Inventor in Connellsville, Pa. The objective of the breeding program is to create new freely-branching and freely-flowering Ivy *Geranium* cultivars with attractive foliage and flower coloration.

The new Ivy *Geranium* originated from a cross-pollination made by the Inventor on Jan. 23, 2004 in Connellsville, Pa. of the *Pelargonium peltatum* cultivar Global Pink Pearl, disclosed in U.S. Plant Pat. No. 12,558, as the female, or seed, parent with the *Pelargonium peltatum* cultivar Global Red, disclosed in U.S. Plant Pat. No. 14,115, as the male, or pollen, parent. The cultivar Oglger14010 was discovered and selected by the Inventor as a flowering plant from within the progeny of the stated cross-pollination in a controlled environment in Connellsville, Pa. on Mar. 3, 2004.

Asexual reproduction of the new Ivy *Geranium* by vegetative terminal cuttings in a controlled environment in Connellsville, Pa. since Mar. 18, 2006, has shown that the unique features of this new Ivy *Geranium* are stable and reproduced true to type in successive generations.

SUMMARY OF THE INVENTION

The cultivar Oglger14010 has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Oglger14010'. These characteristics in combination distinguish 'Oglger14010' as a new and distinct cultivar of Ivy *Geranium:*

1. Outwardly spreading plant habit.
2. Freely basal branching habit.
3. Freely flowering habit.
4. Double red and pale pink to white bi-colored flowers.
5. Good garden performance.

Plants of the new Ivy *Geranium* differ primarily from plants of the female parent, the cultivar Global Pink Pearl primarily in flower color as plants of the cultivar Global Pink Pearl have intense pink-colored flowers.

Plants of the new Ivy *Geranium* differ primarily from plants of the male parent, the cultivar Global Red primarily in flower color as plants of the cultivar Global Red have red-colored flowers. In addition, plants of the new Ivy *Geranium* are more vigorous than plants of the cultivar Global Red.

Plants of the new Ivy *Geranium* can be compared to plants of the *Pelargonium peltatum* cultivar Lulumex, disclosed in U.S. Plant Pat. No. 13,022. In side-by-side comparisons conducted in Connellsville, Pa., plants of the new Ivy *Geranium* differed from plants of the cultivar Lulumex in the following characteristics:

1. Plants of the new Ivy *Geranium* were more vigorous than plants of the cultivar Lulumex.
2. Plants of the new Ivy *Geranium* and the cultivar Lulumex differed in flower color as plants of the cultivar Lulumex had purple and white bi-colored flowers.

BRIEF DESCRIPTION OF THE PHOTOGRAPH

The accompanying colored photograph illustrates the overall appearance of the new Ivy *Geranium*, showing the colors as true as it is reasonably possible to obtain in colored reproductions of this type. Colors in the photograph may differ slightly from the color values cited in the detailed botanical description which accurately describe the colors of the new Ivy *Geranium*. The photograph comprises a side perspective view of a typical flowering plant of 'Oglger14010' grown in a container.

DETAILED BOTANICAL DESCRIPTION

The aforementioned photograph and following observations, measurements and values describe plants grown in Connellsville, Pa. in a glass-covered greenhouse during the summer and under conditions which closely approximate commercial production. During the production of the plants, day temperatures ranged from 21° C. to 32° C., night temperatures ranged from 17° C. to 21° C. and light levels ranged from 2,500 lux to 3,000 lux. Plants were about six months old when the photographs and the description were taken. In the detailed description, color references are made to The Royal Horticultural Society Colour Chart, 2001 Edition, except where general terms of ordinary dictionary significance are used.

Botanical classification: *Pelargonium peltatum* cultivar Oglger14010.

Parentage:

*Female, or seed, parent.*—*Pelargonium peltatum* cultivar Global Pink Pearl, disclosed in U.S. Plant Pat. No. 12,558.

*Male or pollen parent.*—*Pelargonium peltatum* cultivar Global Red, disclosed in U.S. Plant Pat. No. 14,115.

Propagation:

*Type.*—By vegetative terminal cuttings.

*Time to initiate roots, summer.*—About 10 days at temperatures of 20° C.

*Time to initiate roots, winter.*—About 14 days at temperatures of 16° C.

*Time to produce a rooted young plant, summer.*—About 28 days at temperatures of 20° C.

*Time to produce a rooted young plant, winter.*—About 28 days at temperatures of 16° C.

*Root description.*—Fine, fibrous; white in color.

*Rooting habit.*—Freely branching.

Plant description:

*General appearance.*—Outwardly spreading plant habit; uniformly mounded; densely foliated.

*Growth and branching habit.*—Moderately vigorous growth habit. Freely basal branching habit.

*Plant height, to top of foliar plane.*—About 21.7 cm to 26.2 cm.

*Plant height, to top of umbels.*—About 27.6 cm to 29.8 cm.

*Plant width.*—About 92.5 cm.

*Lateral branches.*—Length: About 9.5 cm to 19.8 cm. Diameter: About 3 mm to 5 mm. Internode length: About 2.1 cm to 3.9 cm. Texture: Slightly pubescent. Strength: Strong. Color: 146C.

Foliage description:

*Arrangement.*—Alternate; simple.

*Length.*—About 2.3 cm to 8.4 cm.

*Width.*—About 3.2 cm to 7.2 cm.

*Shape.*—Reniform.

*Apex.*—Acute.

*Base.*—Cordate.

*Margin.*—Pedately-lobed.

*Venation pattern.*—Palmate.

*Texture, upper and lower surfaces.*—Slightly pubescent.

*Color.*—Developing and fully expanded foliage, upper surface: 143A; venation, 141B. Developing and fully expanded foliage, lower surface: 139C; venation, 139C. Zonation pattern: Not observed. Petiole: Length: About 2 cm to 2.2 cm. Diameter: About 1 mm to 1.5 mm. Texture, upper and lower surfaces: Smooth, glabrous. Color, upper and lower surfaces: 144A.

Flower description:

*Flower arrangement.*—Double rotate flowers arranged in rounded hemispherical umbels arising from apical leaf axils. Umbels displayed above the foliage on strong peduncles. Flowers face upright to outward; flowers slightly cupped, becoming more flat with development. Flowers not persistent. Flowers not fragrant.

*Quantity of flowers.*—Freely flowering habit; about five to eight flowers per umbel.

*Flowering season.*—Year-round under greenhouse conditions. In Connellsville, Pa., flowering is continuous from spring until frost in autumn.

*Flower longevity.*—Individual flowers last about 10 to 14 days on the plant.

*Umbel height.*—About 2.9 cm to 3.5 cm.

*Umbel diameter.*—About 6.7 cm to 8.5 cm.

*Flower diameter.*—About 2.3 cm to 4.6 cm.

*Flower depth* (*height*).—About 9 mm to 14 mm.

*Flower buds.*—Length: About 2.6 cm to 3.4 cm. Diameter: About 4 mm to 8 mm. Shape: Elliptical. Color: Close to 144A.

*Petals.*—Quantity per flower: About 10 to 12. Length: About 2.6 cm to 2.8 cm. Width: About 1.3 cm to 1.5 cm. Shape: Ovate. Apex: Rounded. Base: Attenuate. Margin: Entire. Texture, upper and lower surfaces: Smooth, glabrous. Color: When opening and fully opened, upper surface: Close to N155B; towards the margins, 53B to 53C; streaks, 53C; towards the base, speckling, 46C; venation, 53D. When opening and fully opened, lower surface: Close to N155B; towards the margins, darker than 51A or 46C; towards the base, speckling, darker than 51A or 46C; venation similar to lamina.

*Petaloids.*—Quantity per flower: None to about two. Length: About 6 mm to 9 cm. Width: About 3 mm to 6 mm. Shape: Narrowly ovate. Apex: Rounded. Base: Attenuate. Margin: Entire. Texture, upper and lower surfaces: Smooth, glabrous. Color: When opening and fully opened, upper surface: Close to N155B; towards the margins, 53B to 53C; streaks, 53C; towards the base, speckling, 46C; venation, 53D. When opening and fully opened, lower surface: Close to N155B; towards the margins, darker than 51A or 46C; towards the base, speckling, darker than 51A or 46C; venation similar to lamina.

*Sepals.*—Quantity per flower: Five, arranged in a single whorl. Length: About 1 cm. Width: About 2 mm. Shape: Lanceolate. Apex: Acute. Base: Attenuate. Margin: Entire. Color, upper and lower surfaces: Close to 144A.

*Peduncle* (*umbel stem*).—Length: About 11.6 cm to 15.1 cm. Diameter: About 2 mm to 3.5 mm. Strength: Strong. Texture: Smooth, glabrous; leathery. Color: 144A.

*Pedicel* (*individual flower stem*).—Length: About 1.8 cm to 2.1 cm. Diameter: About 1 mm to 2 mm. Strength: Moderately strong. Texture: Smooth, glabrous. Color: 144B.

*Reproductive organs.*—Androecium: Stamen quantity per flower: About six to eight. Filament length: About 5 mm to 9 mm. Filament color: N155B. Anther length: About 1.5 mm to 2 mm. Anther shape: Oval. Anther color: 156D. Pollen amount: Moderate to abundant. Pollen color: 170B. Gynoecium: Pistil quantity per flower: One. Pistil length: About 9 mm. Stigma shape: Split into six parts. Stigma size: About 2.5 mm. Stigma color: 178B. Style length: About 2.5 mm. Style color: 157A. Ovary color: 145D.

*Seed.*—Seed development has not been observed.

Disease/pest resistance: Plants of the new Ivy *Geranium* have not been observed to be resistant to pathogens and pests common to Ivy *Geraniums.*

Garden performance: Plants of the new Ivy *Geranium* have been observed to tolerate rain, wind, and temperatures ranging from about 1° C. to about 35° C. and have demonstrated good garden performance.

It is claimed:

1. A new and distinct variety of Ivy *Geranium* plant, named 'Oglger14010', as illustrated and described.

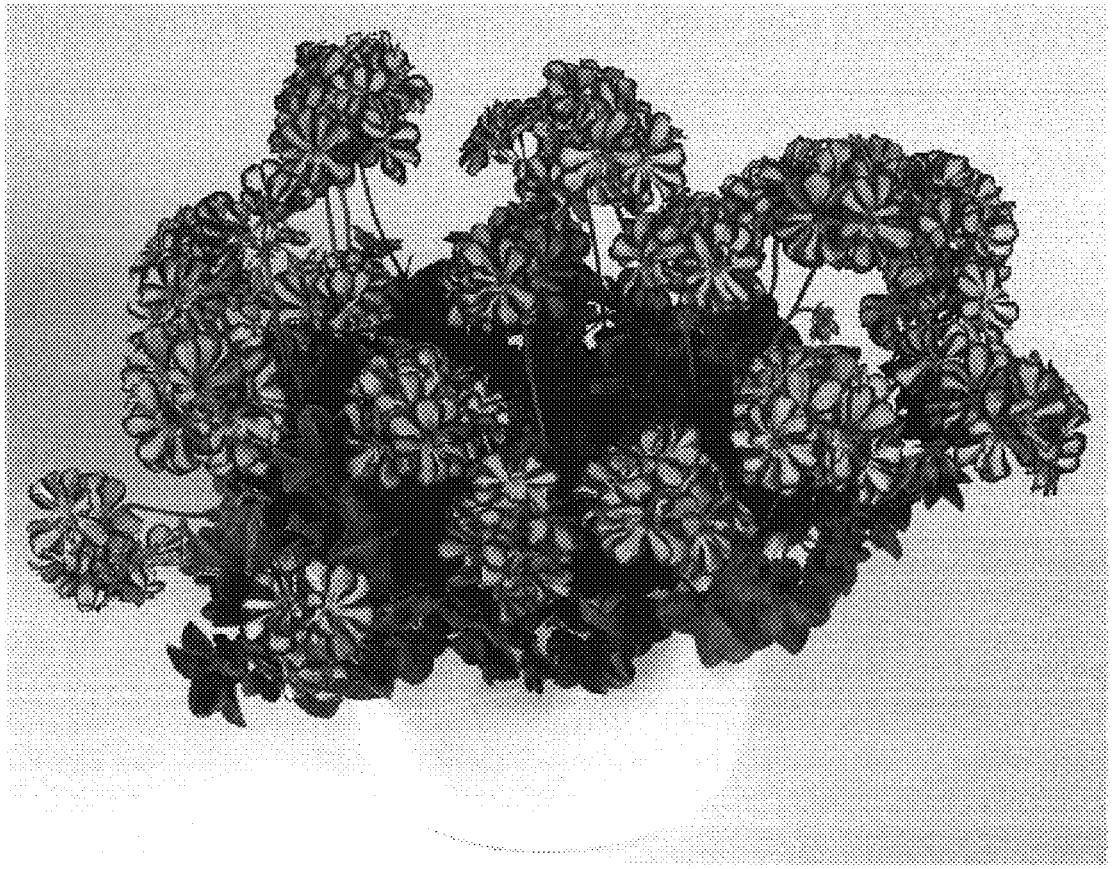

* * * * *